United States Patent
Wang et al.

(10) Patent No.: US 10,405,820 B2
(45) Date of Patent: Sep. 10, 2019

(54) REAL-TIME IMAGE PROCESSING FOR FLUOROSCOPIC IMAGING

(71) Applicant: Carestream Health, Inc., Rochester, NY (US)

(72) Inventors: Xiaohui Wang, Pittsford, NY (US); Samuel Richard, Rochester, NY (US); David H. Foos, Webster, NY (US)

(73) Assignee: Carestream Health, Inc., Rochester, NY (US)

( * ) Notice: Subject to any disclaimer, the term of this patent is extended or adjusted under 35 U.S.C. 154(b) by 610 days.

(21) Appl. No.: 15/164,975

(22) Filed: May 26, 2016

(65) Prior Publication Data

US 2017/0340302 A1    Nov. 30, 2017

(51) Int. Cl.
*A61B 6/00* (2006.01)
*H04W 4/70* (2018.01)

(52) U.S. Cl.
CPC ............ *A61B 6/487* (2013.01); *A61B 6/4405* (2013.01); *A61B 6/461* (2013.01); *A61B 6/467* (2013.01); *A61B 6/5211* (2013.01); *A61B 6/54* (2013.01); *A61B 6/563* (2013.01); *H04W 4/70* (2018.02); *A61B 6/5258* (2013.01)

(58) Field of Classification Search
CPC ....... A61B 6/461; A61B 6/487; A61B 6/5211; A61B 6/54; A61B 6/563; A61B 6/467; A61B 6/5258; A61B 6/542
See application file for complete search history.

(56) References Cited

U.S. PATENT DOCUMENTS

| | | |
|---|---|---|
| 6,332,014 B1 | 12/2001 | Boutenko et al. |
| 6,368,269 B1 | 4/2002 | Lane |
| 7,751,523 B2 | 7/2010 | Ohishi |
| 7,848,560 B2 | 12/2010 | Wang et al. |
| 2004/0125920 A1* | 7/2004 | Zaiki .............. A61B 6/0457 378/195 |
| 2006/0092160 A1 | 5/2006 | Drexler et al. |
| 2006/0203966 A1* | 9/2006 | Mollus ............... A61B 6/06 378/150 |
| 2009/0190718 A1* | 7/2009 | Fan .................. A61B 6/4283 378/102 |
| 2009/0190818 A1 | 7/2009 | Huo |
| 2010/0092061 A1* | 4/2010 | Chen ................... G06T 5/50 382/132 |
| 2013/0044859 A1* | 2/2013 | Yabugami ......... A61B 6/4441 378/62 |
| 2013/0101084 A1* | 4/2013 | Shimizu ............ A61B 6/022 378/42 |
| 2013/0336445 A1* | 12/2013 | Sehnert ............... A61B 6/06 378/42 |
| 2015/0049862 A1 | 2/2015 | Ancar |
| 2016/0275684 A1* | 9/2016 | Elenbaas ........... A61B 6/5247 |

FOREIGN PATENT DOCUMENTS

EP    0 223 296    5/1987

\* cited by examiner

*Primary Examiner* — Chih-Cheng Kao

(57) ABSTRACT

A method for display of a fluoroscopic image sequence during ongoing image acquisition acquires and renders a first image of a subject on a display according to a first parameter setting, modifies the first parameter setting according to an operator instruction entered following acquisition of the first image, and applies the modified first parameter setting for acquiring and rendering one or more subsequent fluoroscopic images of the subject in the fluoroscopic image sequence.

22 Claims, 9 Drawing Sheets

REAL-TIME IMAGE PROCESSING FOR FLUOROSCOPIC IMAGING

TECHNICAL FIELD

The invention relates generally to the field of medical imaging, and in particular to fluoroscopic imaging having image processing for adaptive enhancement of anatomical and artificial features.

BACKGROUND

Fluoroscopic imaging allows real-time viewing of internal anatomy of a patient, allowing an attending practitioner to observe internal features of the patient, including movement within organs and fluid travel. Fluoroscopy imaging is useful for a number of functions related to diagnosis, therapy, and image-guided surgery, for example. Conventionally provided using dedicated systems having an x-ray source and detector on a C-arm or other fixture located within a dedicated radiology/radiography site, fluoroscopic imaging is now being considered for more portable, bedside use, with a digital radiography (DR) detector that is mechanically uncoupled from the radiation source.

Along with developments that are changing the conventional design approaches used for imaging hardware, there is also interest in addressing a number of imaging limitations of conventional fluoroscopy. Fluoroscopy imaging has been characterized as generating images with relatively high noise levels and has often been constrained from accurate presentation of detail for particular structures. There is typically little flexibility available to allow the viewer of the fluoroscopy image to enhance or suppress particular details in the image or to alter the overall presentation of the fluoroscopy image sequence.

One concern for effective patient treatment relates to the ability to detect the proper positioning of tubes that have been inserted into the patient. These include, for example, endo-tracheal (ET) tubes, FT tubes, and NT tubes as well as various types of catheters and endoscopic devices. Proper tube positioning can help to insure delivery or disposal of liquids and gases to and from the patient during a treatment procedure. Improper tube positioning can cause patient discomfort, render a treatment ineffective, or can even be life-threatening. However, even though tubing, wires, and other apparatus used to support the patient can appear in a fluoroscopic image, it can be difficult to visualize these devices clearly. Little or no attention has been paid to offering the capability to temporarily enhance the imaging presentation of tubing and related features in order to support patient treatment.

A difficulty inherent to the fluoroscopy environment relates to the need to manipulate a catheter or other device while, at the same time, referring to the fluoroscopy display for guidance. During a procedure, the practitioner may not be able to reach or to manipulate controls that effect display presentation during the session. Thus, at best, the practitioner must work with the same display settings throughout the exam, even where adjustment would be helpful for improved visibility.

Thus, it can be appreciated that there would be benefits to providing operator-adjustable levels of image enhancement for fluoroscopy imaging.

SUMMARY

Certain embodiments described herein address the need for improved presentation of fluoroscopy images to the viewer. Embodiments of the present invention allow a practitioner to see different treatments of the same imaging content, as well as to adjust image enhancements for improved visibility of particular features.

According to an aspect of the present disclosure, there is provided a method for display of a fluoroscopic image sequence during ongoing image acquisition, the method executed at least in part by a computer and comprising: acquiring and rendering a first image of a subject on a display according to a first parameter setting; modifying the first parameter setting according to an operator instruction entered following acquisition of the first image; and applying the modified first parameter setting for acquiring and rendering one or more subsequent fluoroscopic images of the subject in the fluoroscopic image sequence.

These aspects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings.

The elements of the drawings are not necessarily to scale relative to each other.

DETAILED DESCRIPTION OF THE EMBODIMENTS

Figure 1:
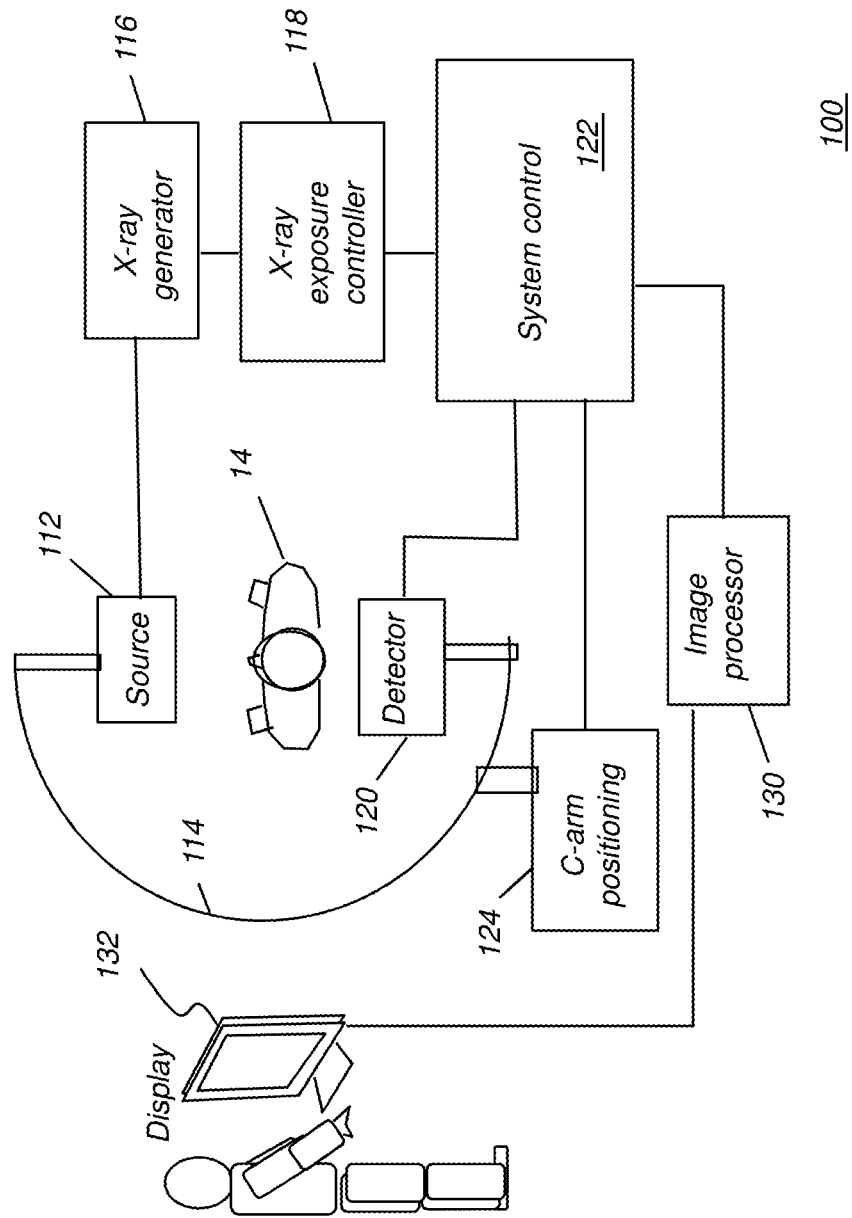
FIG. 1 is a schematic diagram showing a conventional fluoroscopy apparatus.

The following is a detailed description of embodiments of the invention, reference being made to the drawings in which the same reference numerals identify the same elements of structure in each of the several figures.

Where they are used in the context of the present disclosure, the terms "first", "second", and so on, do not necessarily denote any ordinal, sequential, or priority relation, but are simply used to more clearly distinguish one step, element, or set of elements from another, unless specified otherwise.

As used herein, the term "energizable" relates to a device or set of components that perform an indicated function upon receiving power and, optionally, upon receiving an enabling signal.

In the context of the present disclosure, the phrase "in signal communication" indicates that two or more devices and/or components are capable of communicating with each other via signals that travel over some type of signal path. Signal communication may be wired or wireless. The signals may be communication, power, data, or energy signals. The signal paths may include physical, electrical, magnetic, electromagnetic, optical, wired, and/or wireless connections between the first device and/or component and second device and/or component. The signal paths may also include additional devices and/or components between the first device and/or component and second device and/or component.

In the context of the present disclosure, the term "coupled" is intended to indicate a mechanical association, connection, relation, or linking, between two or more components, such that the disposition of one component affects the spatial disposition of a component to which it is coupled. For mechanical coupling, two components need not be in direct contact, but can be linked through one or more intermediary components.

In the context of the present disclosure, the terms "viewer", "operator", and "user" are considered to be equivalent and refer to the viewing practitioner or other person who views and manipulates an x-ray or fluoroscopy image on a display monitor.

As has been described in the background section of the present application, there is a desire to provide the capability to readily switch between different imaging treatments of the fluoroscopy image in order to allow improved visibility of particular features, such as tubes and instruments, and to allow operator-adjustable enhancement of fluoroscopy presentation.

Reference is hereby made to the following: U.S. Pat. No. 7,848,560 (Wang), U.S. 2009/0190818 (Huo), U.S. Pat. No. 7,751,523 (Ohishi), U.S. Pat. No. 6,368,269 (Lane), U.S. 2006/0092160 (Drexler), U.S. Pat. No. 6,332,014 (Boutenko), and EP 0 223 296 A1 (van Woezik).

System Hardware

The block diagram of FIG. 1 shows components of a conventional fluoroscopy imaging apparatus 100. A radiation source 112 and detector 120 are mounted on a C-arm 114 that allows adjustable positioning about a patient 14 or other subject. Source 112 is supplied by an X-ray generator 116, controlled by an exposure controller 118. A system controller 122 coordinates x-ray generation and image acquisition timing, along with positioning of the C-arm 114 by control of a C-arm transport 124. An image processor 130 obtains and processes the acquired image data and presents the fluoroscopy image sequence on a display 132. In the conventional apparatus 100, detector 120 can include an image intensifier tube or other component that connects to controller 122.

Figure 2:
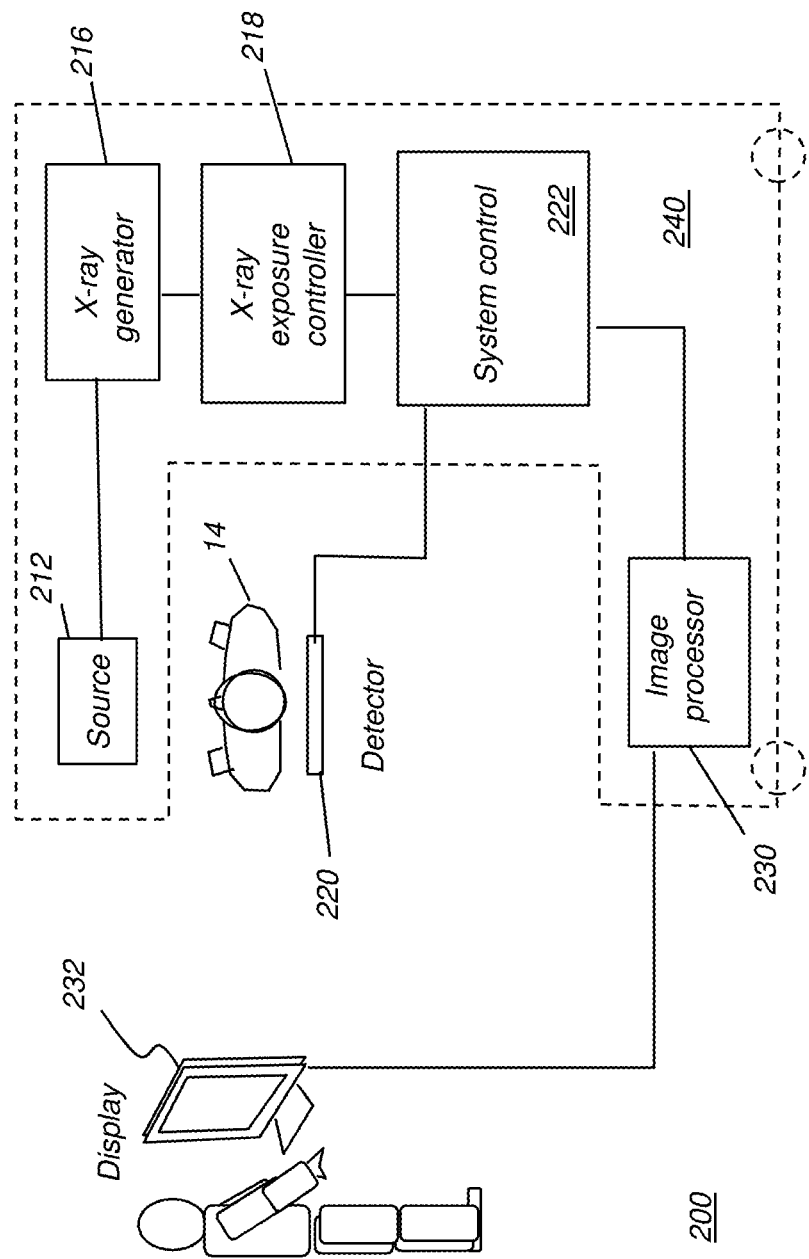
FIG. 2 is a schematic diagram showing a portable fluoroscopy apparatus.

The block diagram of FIG. 2 shows some of the components of a portable fluoroscopy imaging apparatus 200. In this configuration, a detector 220 is a digital radiography DR detector that is mechanically uncoupled from the x-ray source 212. DR detector 220, placed beneath or to the side of the patient 14, communicates through a cabled or wireless connection to a system controller 222. A dashed outline indicates components that can be part of a portable radiographic imaging system 240, such as a portable radiography apparatus that can be wheeled between different locations within a hospital or other medical facility. System 240 can include an X-ray generator 216, and an X-ray exposure controller 218 under control by system controller 222. An image processor 230, in signal communication with system controller 222, then performs the needed image processing on the fluoroscopy image sequence and presents the processed image content for the subject on a display 232 that can be part of the portable system 240 or can be a separately provided device that is in signal communication with image processor 230.

Components not shown in the simplified schematic diagrams of FIGS. 1 and 2 can include supporting hardware for transport, power, network connection to storage devices, and other standard components provided with or available to radiographic imaging systems.

Fluoroscopy apparatus such as those shown in FIGS. 1 and 2 acquire, process, and render or display successive images of a patient or other type of subject in rapid sequence. The displayed content has the appearance of video display as the image sequence is rendered to the display. Fluoroscopy imaging is advantaged in being capable of showing motion of and within internal anatomy. Conditioning of the image content in the ongoing fluoroscopy sequence must be performed at high speeds and is typically performed equivalently for all images in the sequence.

In general, there is a proportional relationship between radiation dose levels and image processing. The higher the dose, the more detail available for image processing. Thus, image processing can have increased density of information at higher dose and image processing algorithms and techniques can take advantage of this increased density by using more aggressive parameters, with extended inherent dynamic range and other characteristics, for example.

Multi-Band Spatial Frequency Enhancement

Figure 3B:
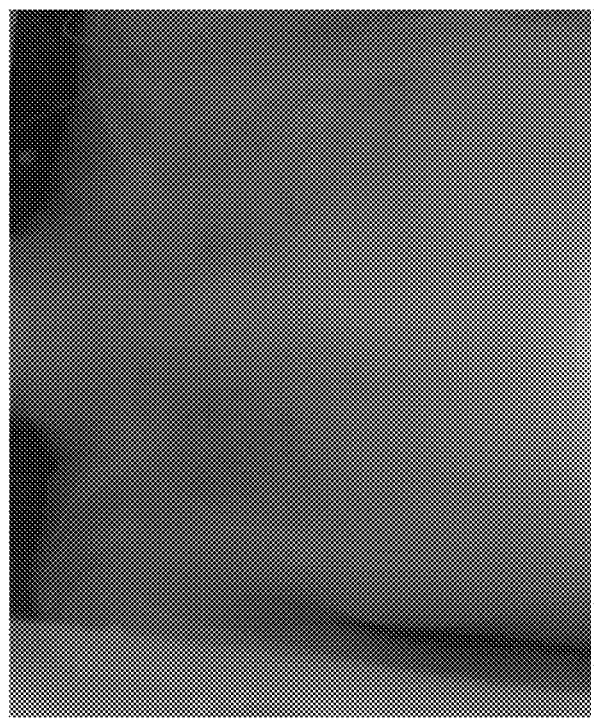
FIG. 3B shows an image for the same or similar anatomy showing the effects of multi-band spatial frequency decomposition.
Figure 3A:
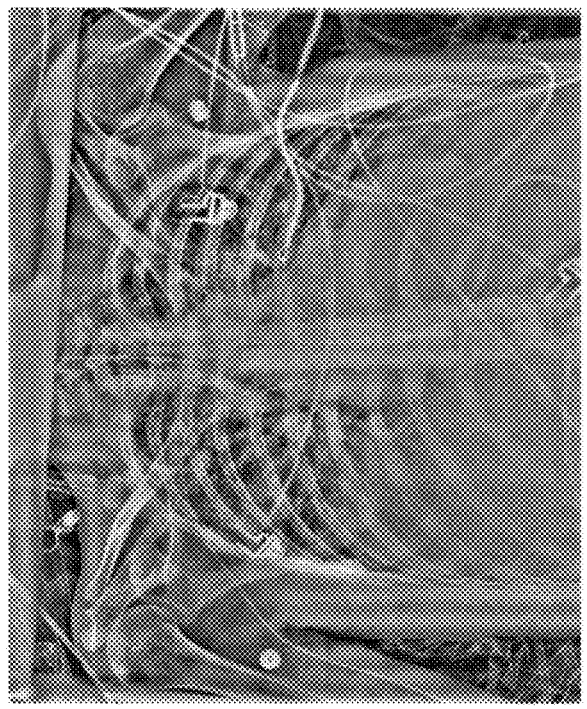
FIG. 3A shows a conventional fluoroscopy image, exhibiting high noise content and low contrast.

Improved contrast and noise suppression, with enhancement of treatment apparatus such as catheters and other types of endoscopic devices, tubing, lines, and blood vessels, as well as various types of contrast media, would be advantageous for a number of fluoroscopy imaging applications, even when applied selectively, such as at different intervals during a procedure. According to an embodiment of the present disclosure, multi-band spatial frequency decomposition and subsequent re-composition can be used to enhance image quality of the fluoroscopic imaging sequence. By way of example, FIG. 3A shows a conventional fluoroscopy image, exhibiting high noise content and low contrast. FIG. 3B shows an image for the same or similar anatomy showing the effects of multi-band spatial frequency decomposition.

Figure 4:
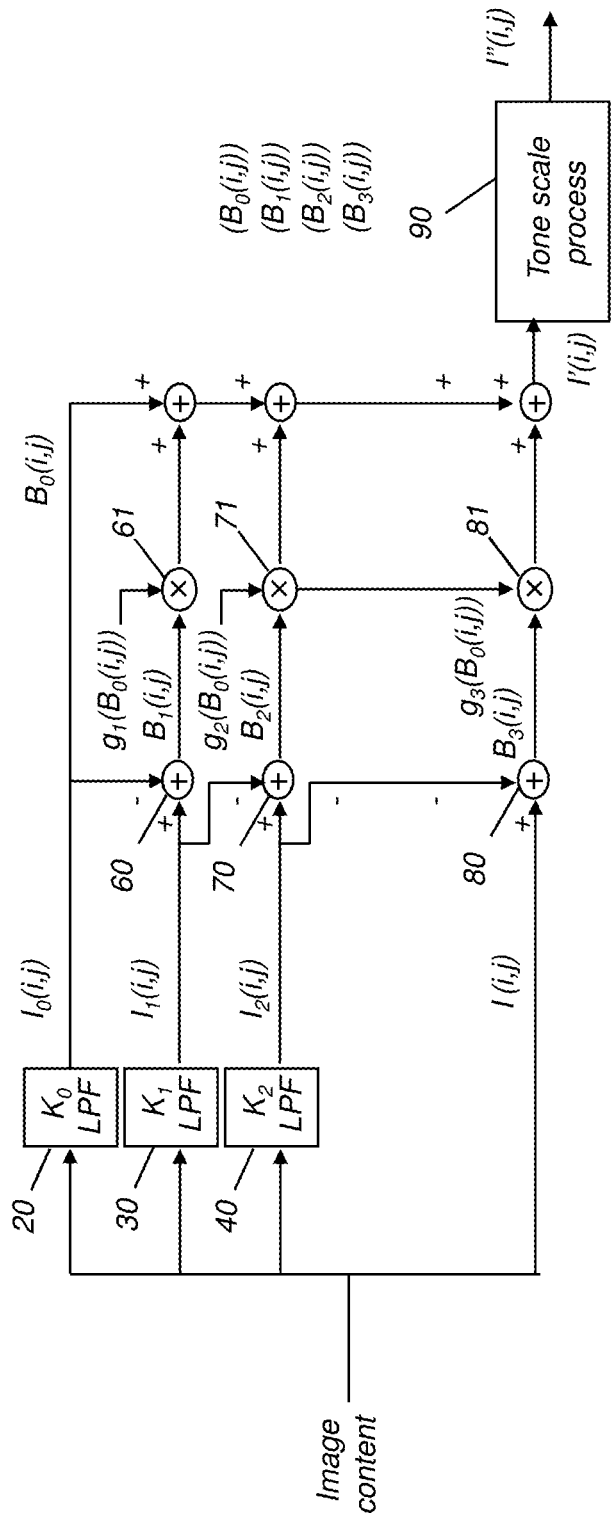
FIG. 4 shows an image processing schema for manipulation of individual frequency bands of an image using multi-band spatial frequency decomposition and recomposition.

The block diagram of FIG. 4 shows an image processing schema for manipulation of individual frequency bands in rendering an image using multi-band spatial frequency decomposition and recomposition. A processing method applying such a schema can be used to achieve desired levels of dynamic range compression, along with various contrast and detail enhancements such as tube and line enhancement, noise suppression, contrast media enhancement, and other conditioning for successive images obtained in a fluoroscopic imaging series or sequence.

In each acquired digital image, each code value in the image content, obtained and used by the imaging system for subsequent processing, is linearly related to log exposure captured by the fluoroscopy detector (120 in FIG. 1; 220 in FIG. 2). The processing shown in FIG. 4 conditions the log exposure code value data in a series of individual frequency bands, shown in this example as four frequency bands $B_0(i,j)$, $B_1(i,j)$, $B_2(i,j)$, and $B_3(i,j)$. The log exposure code value data I(i,j) of the input digital image is first processed by three different low-pass filter (LPF) operators 20, 30, and 40. Each operator can use a square-wave filter. It will be evident to those skilled in the art that other low-pass filter shapes such as a triangle-filter can be used. The filter kernel sizes are chosen to manipulate different sized features (or different frequency ranges) in the image.

The first low-pass filter operator 20 uses kernel $K_0$. This operator uses the largest kernel size and it passes only the lowest frequencies. It generates the low-pass image $I_0(i,j)$. The next low-pass operator 30 uses kernel $K_1$. This operator uses the next largest kernel size and it passes the low to mid frequencies. It generates the low-pass image $I_1(i,j)$. The final low-pass operator 40 in this example uses kernel $K_2$. This operator uses the smallest kernel size and it passes all frequencies except for the very highest. This kernel generates the low-pass image $I_2(i,j)$. It can be appreciated that different intermediate frequency bands can be added to the schema of FIG. 4 as needed, following the basic pattern shown.

The low-pass images are used to generate the frequency bands. The lowest frequency band image is $B_0(i,j)$ and is equal to $I_0(i,j)$. This band represents large-sized features in the image (and contains the lowest frequencies). Manipulation of this band produces a change in dynamic range or latitude.

The next frequency band $B_1(i,j)=I_1(i,j)-I_0(i,j)$ is generated by a subtractor 60. This band contains the low-to-mid frequencies and represents mid-sized features in the image. Manipulation of this $B_1(i,j)$ band produces a contrast effect without noticeably affecting the overall dynamic range.

The next frequency band $B_2(i,j)=I_2(i,j)-I_1(i,j)$ is generated by a subtractor 70. This band contains the mid-to-high frequencies and represents the small-sized features and detailed content of the image. Manipulation of this $B_2(i,j)$ band produces a sharpness or blurring effect of the small-sized features. The next frequency band $B_3(i,j)=I(i,j)-I_2(i,j)$ is generated by a subtractor 80. This band contains the highest frequencies in the image and represents very fine detail in the image. Manipulation of the $B_3(i,j)$ band produces a sharpness or blurring effect of very fine detail in the image.

As shown further in FIG. 4, the higher frequency bands $B_1(i,j)$, $B_2(i,j)$, and $B_3(i,j)$ are multiplied by respective gain terms $g_1(B_0(i,j))$, $g_2(B_0(i,j))$, $g_3(B_0(i,j))$ at respective multipliers 61, 71, 81 and summed together with the lowest frequency band image $B_0(i,j)$ to generate the reconstructed image using I'. The reconstructed image I' is defined as follows:

$$I'(i,j)=B_0(i,j)+g_1(B_0(i,j))*B(i,j)+g_2(B_0(i,-j))*B_2(i,j)+g_3(B_0(i,j))*B_3(i,j)$$

If the bands are not manipulated, that is, if:

$$g_1(B_0(i,j))=g_2(B_0(i,j))=g_3(B_0(i,j))=1.0,$$

the reconstructed image I' is equal to the original image I, i.e., I'(i,j)=I(i,j).

As shown in FIG. 4 the reconstructed image I' is mapped through a tone scale (TS) process 90 which maps the values into the desired display range. The output image is represented as I''(i,j)=TS(I'(i,j)).

Advantageously, image frequency decomposition and recomposition can be executed quickly, allowing real-time display of conditioned fluoroscopy images having the same dynamic range and other characteristics. Coefficients for gain values, for example, can be parameters readily assigned and modified according to operator instructions. These parameter values can then be used in the image processing chain.

Figure 5:
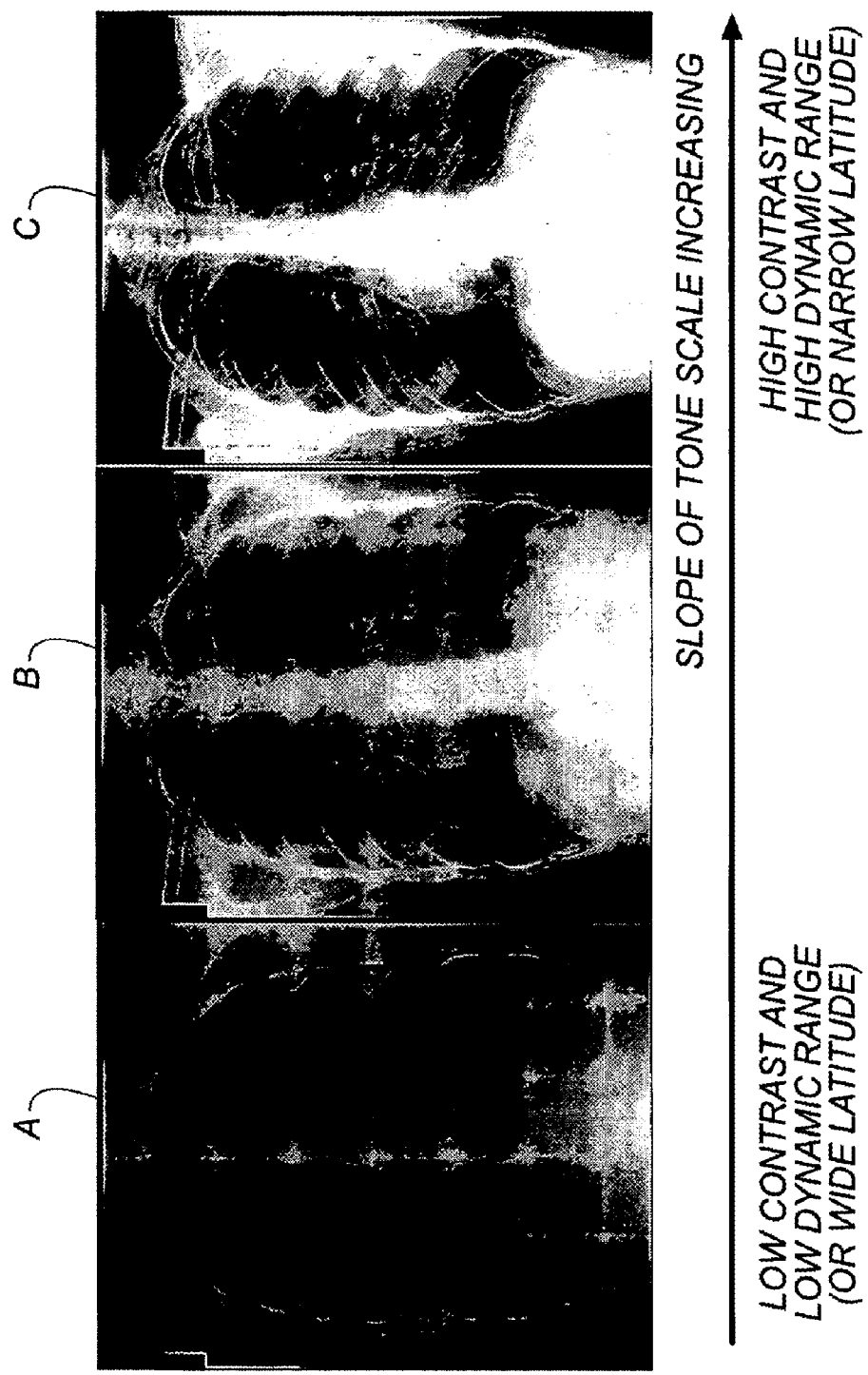
FIG. 5 shows the use of multi-band spatial frequency decomposition and recomposition for contrast and dynamic range adjustment.

Among image conditioning that can be performed using multi-band spatial frequency decomposition and recomposition are contrast and dynamic range, for example, as shown in FIG. 5.

Figure 6:
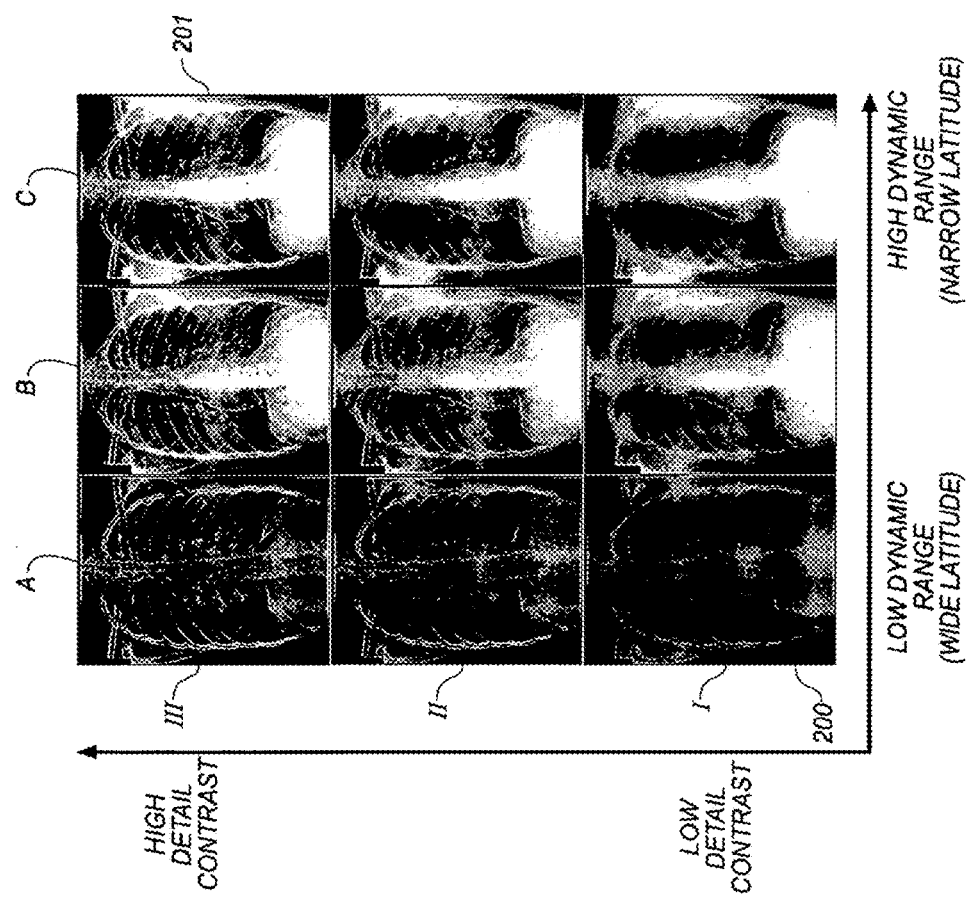
FIG. 6 shows how independent control of dynamic range and detail contrast can be obtained using multi-band spatial frequency decomposition and recomposition.

By way of further example, FIG. 6 shows how independent control of dynamic range and detail contrast can be obtained using multi-band spatial frequency decomposition and recomposition. The operator can be presented with an initial fluoroscopy image, or a scout image, showing image treatments with varying levels of detail contrast and dynamic range for selection. The selection made by the operator can then be used to provide parameter settings for use by the image processing logic and applied to subsequent images in the fluoroscopy sequence.

Alternate or additional image processing can include dynamic range compression with temporal averaging, such as averaging based on the fluoroscopy frame rate. Temporal averaging based on the acquisition rate, for example, can help to reduce noise and flicker.

Processing Sequence

According to an embodiment of the present disclosure, the image processing settings for a fluoroscopy imaging sequence is set up using either the first obtained image for the sequence or using a scout image that is acquired solely for the purpose of adjustment setting. Analysis of the initial image then enables the selection of suitable image processing parameters for the images obtained subsequently.

Image processing for the sequence can be automatic or can allow adjustment by the viewer, accepting adjustments to image processing parameters, modifying settings for characteristics such as brightness, contrast, dynamic range, noise suppression, or other attributes.

According to an alternate embodiment of the present disclosure, the viewer can be presented with a simulated fluoroscopy sequence using only a single image or a small set of initial images. The viewer is presented with a series of different simulations for noise content. The viewer can then specify an acceptable noise level for viewing; this selection then determines x-ray source technique settings (including mA and kV settings, filter settings, and pulse width, for example) as well as image processing preferences.

Toggling Between Image Processing Variants

Figure 7A:
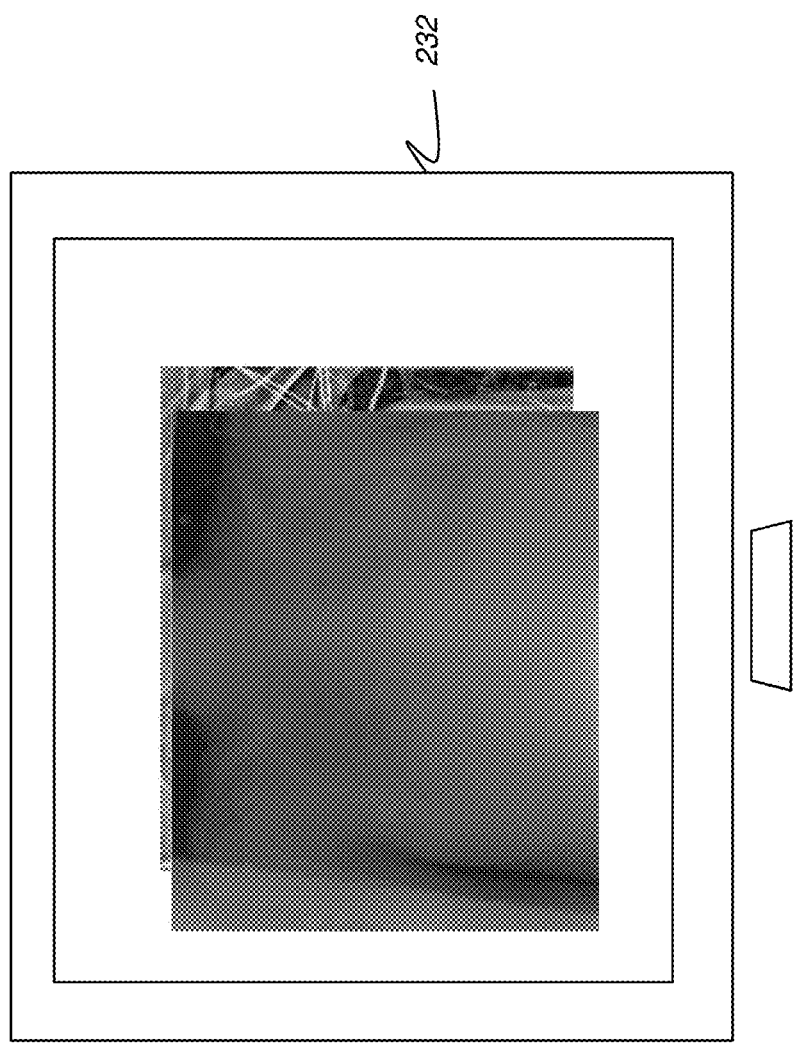
FIGS. 7A and 7B show two different treatments of the same image anatomy from a simulated fluoroscopy system.
Figure 7B:
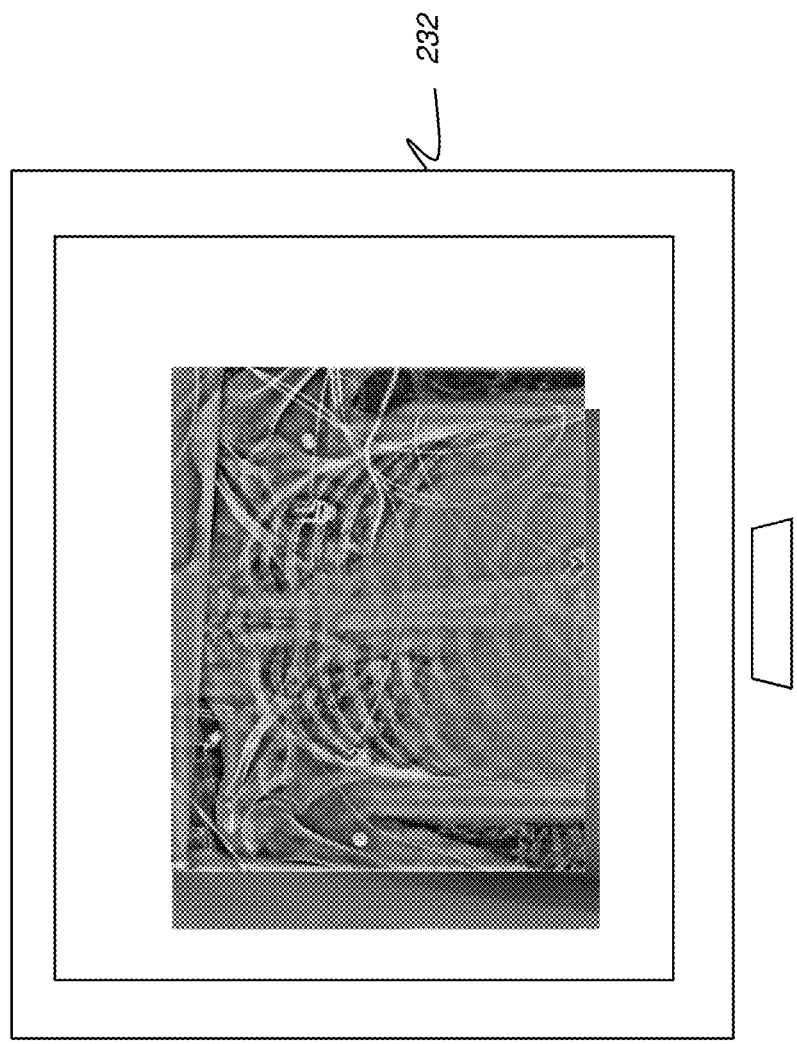

According to an embodiment of the present disclosure, the fluoroscopy viewer has the option to toggle between different image conditioning, allowing the viewer to take advantage of different image treatments according to what might be most useful at a particular time during a procedure. FIGS. 7A and 7B show two different treatments of the same image anatomy from a simulated fluoroscopy system. FIG. 7A shows imaging results using standard fluoroscopy image processing settings. FIG. 7B shows imaging results using enhanced fluoroscopy image processing, such as the multi-band spatial frequency decomposition and recomposition enhancements described with reference to FIG. 4. According to an embodiment of the present disclosure, an operator instruction, entered on a touch screen, keyboard console, foot pedal or control, or using some other input device such a voice recognition apparatus, for example, enables the viewer to toggle between different renderings of the same fluoroscopy image content, such as by changing parameter settings for the fluoroscopy system or for its image processing.

Variable Processing Parameters Under Operator Control

One advantage of multi-band spatial frequency decomposition and recomposition and similar image processing techniques is the capability to adjust the amount of conditioning that is applied to an image or, in the case of fluoroscopy, to an ongoing sequence of images by straightforward adjustment of parameters. Additionally, embodiments of the present disclosure allow the viewer to adjust image processing of the fluoroscopy sequence in real time, so that different features relevant to the practitioner in performing a procedure can be highlighted at different times during the ongoing fluoroscopy sequence. It would be further advantageous to provide a method of adjustment that allows hands-free operation for modifying the appearance of the rendered image, with an intuitive adjustment mechanism that provides real-time response, allowing modification of parameter settings that take effect during the ongoing fluoroscopy session.

Embodiments of the present disclosure not only allow adjustment of image processing parameters by the operator during the fluoroscopy session, but also optionally allow adjustment of system technique settings, such as mA and kV settings or filtration used for the radiography system for obtaining the fluoroscopic image sequence, for example.

Figure 8:
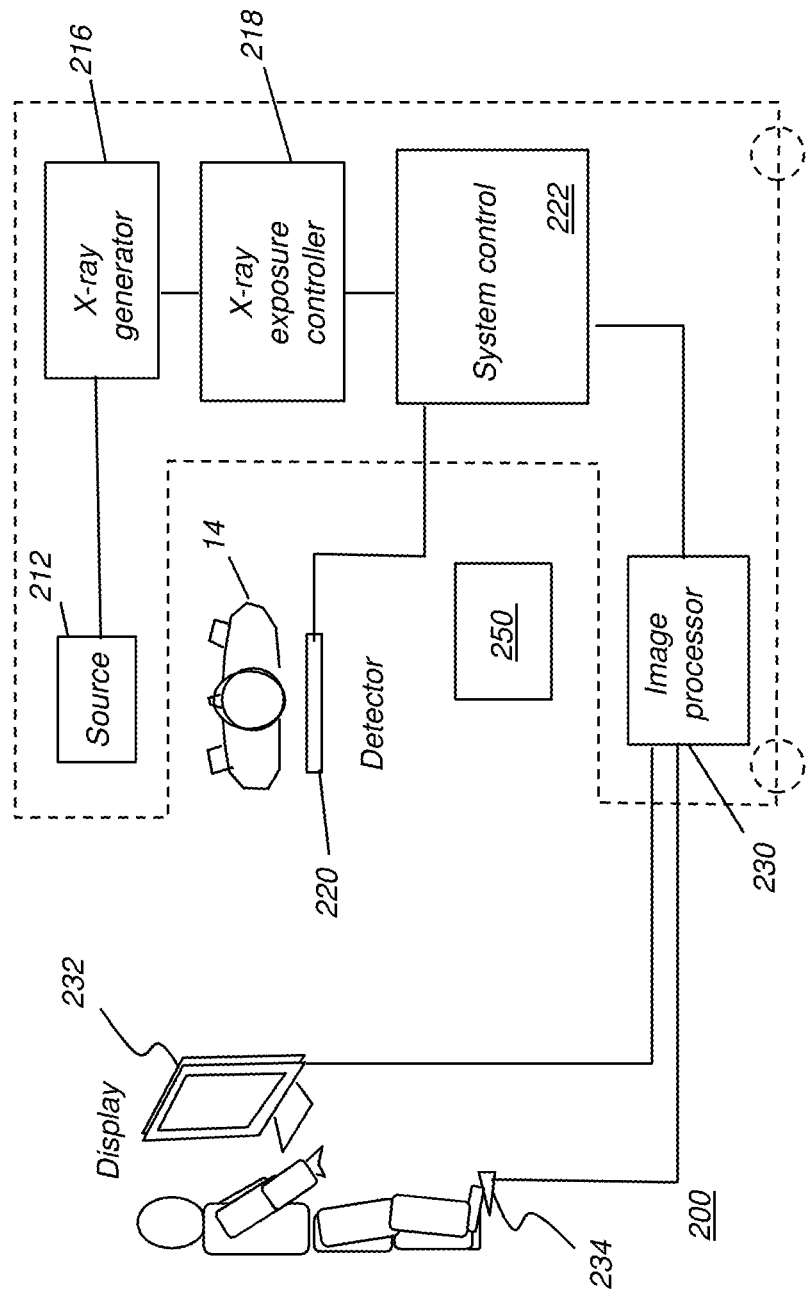
FIG. 8 is a schematic diagram showing components of a portable fluoroscopy apparatus with an operator foot pedal.

The schematic diagram of FIG. 8 shows an embodiment of fluoroscopy imaging apparatus 200 that includes a foot pedal 234 that is in signal communication with system controller 222 or, optionally, with image processor 230. Foot pedal 234 can be a binary toggle, allowing the viewer to switch between standard and enhanced viewing modes, as shown in FIGS. 7A and 7B respectively, for example.

Alternately, foot pedal 234 can be used for adjustment at a number of different levels, including having a set of fixed positions for discrete levels or allowing continuous adjustment based on pedal position. This type of continuous adjustment would allow the viewer to adjust detail contrast, detail visibility, and other imaging factors according to particular content of interest during a procedure, such as while inserting a tube or catheter or other type of treatment apparatus, for example. The foot pedal can also be used to enable and disable x-ray generation. Other types of operator control could alternately be used, such as a touch screen icon, including radio dial or slide bar, for example.

The schematic diagram of FIG. 8 also allows foot pedal 234 to provide a signal for adjusting x-ray output energy, such as by varying the mA or kV values before and during a fluoroscopy procedure. In this embodiment, foot pedal 234 generates signal content to system controller 222 for modulating the x-ray output. Using this capability, the practitioner can set the exposure to different levels for different parts of a procedure, depending on the need for high-resolution, high-contrast detail with correspondingly higher dose or for lower resolution at other times during the procedure.

According to an alternate embodiment, multiple foot pedals can be used, each providing a different image enhancement function. One or more foot pedals can alternately be used with the C-arm fluoroscopy system of FIG. 1, for example, to separately adjust exposure level and image dynamic range at different times during the fluoroscopy imaging session.

Alternate controls can be used for toggling between image processing treatments as well as to adjust the enhancement level during the fluoroscopy imaging session. The operator may, for example, be able to enter commands on the keyboard or use a foot-pedal or other input device such a voice recognition apparatus as preferred during the session.

Foot pedal operation can thus control either or both of the following to modify the appearance of a rendered image:

(i) image processing parameters, providing parameters such as those used to set gain coefficients for different frequency bands of the image, as shown with reference to FIG. 4; and (ii) technique for exposure, such as controlling parameters of mA or kV that adjust the output energy of the x-ray source, for example.

In operation, pressing the foot pedal 234 once can activate the signal generation circuitry of the foot pedal. Then, adjustment of the foot pedal 234 can provide control of either image processing or technique parameters in continuous manner, providing a type of analog control, or in discrete increments, for which different pedal positions have discreet signal values. A threshold value can be set, so that all operator foot pedal adjustments are constrained to within a set of values. Alternately, foot pedal 234 can operate in binary manner, as an on/off switch or display selector, for example. Stepping on foot pedal 234, for example, can begin the exposure for the fluoroscopy exam.

An optional sensor 250 in the FIG. 8 configuration, such as a wireless sensor or a sensor wired to system control 222, can be provided to sense gesture-based commands from the practitioner. Gesture-based or audio commands can be used to provide operator instructions, also allowing hands-free operation for adjusting parameters that modify the appearance of the rendered image.

The invention has been described in detail, and may have been described with particular reference to a suitable or presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. A method for generating fluoroscopic images, the method executed at least in part by a computer, comprising:
    acquiring and rendering a first image of a subject on a display according to a first parameter setting;
    modifying the first parameter setting according to an operator instruction entered following acquiring and rendering of the first image, the step of modifying the first parameter setting comprising:
        filtering a sequence of fluoroscopic images each into a plurality of frequency bands;
        modifying a gain of one of the plurality of frequency bands for each of the fluoroscopic images in the sequence of fluoroscopic images;
    acquiring and processing each of the fluoroscopic images of the sequence according to the modified first parameter setting; and
    rendering, to the display, at least one of the processed fluoroscopic images of the fluoroscopic image sequence.

2. The method of claim 1 wherein the step of rendering comprises recombining the sequence of fluoroscopic images filtered into the plurality of frequency bands including the gain modified fluoroscopic images in the sequence of fluoroscopic images.

3. The method of claim 1 wherein modifying the first parameter setting comprises adjusting an x-ray source technique setting, wherein the technique setting includes at least one of the following: kV, mA, filtration, and pulse width.

4. The method of claim 1 wherein modifying the first parameter setting comprises adjusting (i) a dynamic range for image rendering, or (ii) image contrast.

5. The method of claim 1 wherein modifying the first parameter setting comprises adjusting image data processing (i) to adjust or compress dynamic range, (ii) to enhance detail contrast, or (iii) to suppress noise.

6. The method of claim 1 wherein modifying the first parameter setting comprises enhancing display contrast for at least one treatment apparatus of: tubing, catheters, and wires.

7. The method of claim 1 wherein modifying the first parameter setting comprises enhancing display contrast for a contrast medium.

8. The method of claim 1 further comprises obtaining the operator instruction by acquiring a signal from a foot pedal control.

9. The method of claim 1 further comprising:
providing a foot pedal control for enabling and disabling an x-ray source; and
obtaining the operator instruction by acquiring a signal from the foot pedal control.

10. The method of claim 1 further comprising:
providing a foot pedal control for continuously variably adjusting the first parameter setting; and
obtaining the operator instruction by acquiring a signal from the foot pedal control.

11. The method of claim 1 further comprising:
providing a foot pedal control for adjusting the first parameter setting to one of a set of discrete values; and
obtaining the operator instruction by acquiring a signal from the foot pedal control.

12. The method of claim 1 further comprises obtaining the operator instruction from one of the following: (i) a gesture-based interaction, (ii) a keyboard console, (iii) a touch screen command, or (iv) a voice command/recognition.

13. The method of claim 1 further comprising applying a dynamic range compression with temporal averaging to the one or more subsequent rendered images in the fluoroscopic image sequence.

14. The method of claim 1 wherein modifying the first parameter setting of the first rendered image comprises applying a multi-band spatial frequency adjustment to image data.

15. The method of claim 1 wherein acquiring and rendering the first image comprises acquiring and rendering a scout image.

16. The method of claim 1 wherein rendering the first image further comprises
rendering the first image with simulated noise content at a first level and with simulated noise content at a second level and prompting for an operator selection of the first or second level; and
rendering additional images in the fluoroscopic image sequence according to the operator noise content selection.

17. A method for generating fluoroscopic images, the method executed at least in part by a computer, comprising:
acquiring and rendering a scout image of a subject on a display according to a first parameter setting;
repeating the steps of:
(i) modifying the first parameter setting according to an operator instruction entered using a foot pedal, the step of modifying the first parameter setting comprising:
filtering a sequence of fluoroscopic images each into a plurality of frequency bands;
modifying a gain of one of the plurality of frequency bands for each of the fluoroscopic images in the sequence of fluoroscopic images;
(ii) acquiring and processing each of the fluoroscopic images of the sequence according to the modified first parameter setting; and
(iii) rendering, to the display, one or more processed fluoroscopic images of the fluoroscopic image sequence by combining the fluoroscopic images filtered in the plurality of frequency bands including the gain modified fluoroscopic images.

18. A fluoroscopic imaging apparatus comprising:
a portable radiography apparatus comprising: a system controller, an x-ray exposure controller, and an x-ray generator and x-ray source;
a digital radiography detector mechanically de-coupled from the x-ray source and in signal communication with an image processor;
an operator control for providing a signal to the image processor related to an adjustable parameter setting for fluoroscopic image rendering, wherein the image processor is configured to filter each of fluoroscopic images of a sequence into a plurality of frequency bands, to modify a gain of the fluoroscopic images in a programmably selected one of the frequency bands in response to the operator provided signal, and to recombine the sequence of filtered fluoroscopic images including the gain modified fluoroscopic images in the programmably selected frequency band; and
a display for displaying the rendered fluoroscopic image.

19. The apparatus of claim 18 wherein the operator control is a foot pedal, a wireless gesture-detection apparatus, or a touch screen control.

20. The apparatus of claim 19 wherein the foot pedal has a discrete number of fixed positions.

21. The apparatus of claim 19 wherein the foot pedal provides continuously variable adjustment of image equalization and feature enhancement.

22. The apparatus of claim 18 wherein the digital radiography detector includes a wireless communication system for wireless communication with the image processor.

* * * * *